(12) United States Patent
D'arcy et al.

(10) Patent No.: US 9,339,227 B2
(45) Date of Patent: May 17, 2016

(54) COGNITIVE FUNCTION ASSESSMENT IN A PATIENT

(75) Inventors: Ryan D'arcy, North Vancouver (CA); Donald F. Weaver, Halifax (CA); Sujoy Ghosh Hajra, Halifax (CA); Careesa Liu, Halifax (CA); Lauren Sculthorpe-Petley, Halifax (CA)

(73) Assignee: National Research Council of Canada, Ottawa, ON (CA)

( * ) Notice: Subject to any disclaimer, the term of this patent is extended or adjusted under 35 U.S.C. 154(b) by 535 days.

(21) Appl. No.: 13/701,252

(22) PCT Filed: Jun. 17, 2011

(86) PCT No.: PCT/CA2011/050367
§ 371 (c)(1),
(2), (4) Date: Feb. 15, 2013

(87) PCT Pub. No.: WO2011/160222
PCT Pub. Date: Dec. 29, 2011

(65) Prior Publication Data
US 2013/0245422 A1    Sep. 19, 2013

Related U.S. Application Data

(60) Provisional application No. 61/357,346, filed on Jun. 22, 2010.

(51) Int. Cl.
*A61B 5/05* (2006.01)
*A61B 5/00* (2006.01)
(Continued)

(52) U.S. Cl.
CPC ............ *A61B 5/4842* (2013.01); *A61B 5/04009* (2013.01); *A61B 5/04012* (2013.01); *A61B 5/0484* (2013.01); *A61B 5/04845* (2013.01); *A61B 5/165* (2013.01); *A61B 5/7246* (2013.01)

(58) Field of Classification Search
None
See application file for complete search history.

(56) References Cited

U.S. PATENT DOCUMENTS 4,846,190 A * 7/1989 John .............................. 600/544
5,003,986 A * 4/1991 Finitzo et al. ................. 600/544
(Continued)

FOREIGN PATENT DOCUMENTS

WO    2006009771    1/2006

OTHER PUBLICATIONS

Duffy et al. "Dyslexia: Automated diagnosis by computerized classification of brain electrical activity", Annals of Neurology, vol. 7, issue 5, pp. 421-428, May 1980.
(Continued)

*Primary Examiner* — Long V Le
*Assistant Examiner* — Bradley Impink
(74) *Attorney, Agent, or Firm* — Adrian D. Battison; Ade & Company Inc.

(57) ABSTRACT

A method for analysis of the extent of conscious awareness and likelihood of recovery of a patient includes the steps of applying to the patient a sensory stimulus sequence which is typically auditory; carrying out an EEG to generate waveform signals to record changes in the electromagnetic fields generated by the patient's neural activity; using software provided in a processor to process the waveform signals in order to locate waveform peaks, identify the event-related potential (ERP) components obtained in the waveform and to obtain quantitative measures of those components; and using the software to generate and communicate scores indicative of the extent of conscious awareness and likelihood of recovery of the patient.

11 Claims, 6 Drawing Sheets

(51) Int. Cl.
*A61B 5/0484* (2006.01)
*A61B 5/16* (2006.01)
*A61B 5/04* (2006.01)

(56) References Cited

U.S. PATENT DOCUMENTS

| | | | | |
|---|---|---|---|---|
| 5,611,350 | A * | 3/1997 | John | 600/378 |
| 6,052,619 | A * | 4/2000 | John | 600/544 |
| 6,066,163 | A * | 5/2000 | John | 607/45 |
| 6,223,074 | B1 * | 4/2001 | Granger | 600/544 |
| 6,416,480 | B1 * | 7/2002 | Nenov | 600/557 |
| 2004/0193068 | A1 * | 9/2004 | Burton et al. | 600/544 |
| 2005/0273017 | A1 * | 12/2005 | Gordon | 600/544 |
| 2007/0032737 | A1 * | 2/2007 | Causevic et al. | 600/544 |
| 2010/0076333 | A9 | 3/2010 | Burton et al. | |
| 2010/0227296 | A1 * | 9/2010 | Mandelis et al. | 433/215 |

OTHER PUBLICATIONS

D'arcy et al. "Separating Phonological and Semantic Processing in Auditory Sentence Processing: A High-Resolution Event-Related Brain Patential Study", Human Brain Mapping, vol. 22, pp. 40-51, 2004.

Gawryluk et al. "Improving the clinical assessment of consciousness with advances in electrophysiological and neuroimaging techniques", BioMed Central Neurology 2010, 10:11.

Kotchoubey et al. "Information processing in severe disorders of consciousness: Vegetative state and minimally conscious state", Clinical Neurophysiology pp. 2441-1453, 2005.

Neumann et al. "Assessment of cognitive functions in severely paralysed and severely brain-damaged patients: neuropsychological and electrophysioogical methods", Brain Research Protocols, pp. 25-36, Sep. 3, 2004.

Connolly et al. "The application of cognitive event-related brain potentials (ERPs) in language-impaired individuals: review and case studies", International Journal of Psychophysiology, pp. 55-70, 2000.

Ponton et al. "Integrated mismatch negativity (MMN): a noise-free representation of evoked responses allowing single-point distribution-free statistical tests", Electroencephalography and clinical Neurophysiology, pp. 143-150, 1997.

Rodriguez-Fornells et al. "Electrophysiological estimates of the time course of semanticand phonological encoding during listening and naming", Neuropsychologia, pp. 778-787, 2002.

Sculthorpe et al. "Evidence that the mismatch negativity to pattern violations does not vary with deviant probability", Clinical Neurophysiology, pp. 2236-2245, May 19, 2011.

Sinkkonen et al. "Towards Optimal Recording and Analysis of the Mismatch Negativity", Audiology Neuro-Otology, vol. 5, pp. 235-246, 2000.

\* cited by examiner

Halifax Consciousness Scan
Score: 5/10

| | Dx | Rx | Vx | Px |
|---|---|---|---|---|
| Language | 0/2 | 0/1 | 0/1 | 0% |
| Attention | 2/2 | 1/1 | 1/1 | 20% |
| Memory | 0/2 | 0/1 | 0/1 | 0% |
| Perception | 1/2 | 1/1 | 1/1 | 15% |
| Sensation | 2/2 | 1/1 | 1/1 | 10% |

Name: Barbara Graham
Age: 73    Sex: F
Process Date: April 13, 2010
11:45 am

COGNITIVE FUNCTION ASSESSMENT IN A PATIENT

This application claims the benefit under 35 USC 119 of U.S. Provisional Application 61/357,346 filed Jun. 22, 2010.

This invention relates to a method for cognitive function assessment in a patient.

BACKGROUND OF THE INVENTION

While diagnostic imaging methods such as computerized tomography (CT) and magnetic resonance imaging (MRI) have long been employed by physicians to determine the extent of structural insults to the brain, clinical testing for the functional integrity of brain structures above the brainstem has traditionally been left to the domain of neuropsychology. Neuropsychological assessments typically involve batteries of psychometric and behavioural tests that can only be carried out on awake, alert patients who are capable of providing verbal and behavioural responses. Severe traumatic brain injury (TBI), however, commonly induces unconsciousness and/or paralysis, making standard neuropsychological testing impossible. Unfortunately, this is all too often the case for a host of brain injuries and diseases (e.g., stroke, Alzheimer's disease, Parkinson's Disease, autism, etc). The fundamental problem stems from the dependence on behavioural responses (motor or verbal), which are also invariably affected to some degree by the brain insult. This compromises the ability to conduct an assessment using behavioural responses, rendering them with definable limitations.

Case in point: For many years, the "gold standard" for testing conscious awareness has been the Glasgow Coma Scale (GCS). First reported more than 35 years ago, this long-standing clinical tool has since been followed by more sophisticated measures like the JFK Coma Recovery Scale—Revised. However, all rely on behavioural indications of consciousness. As a result, estimates of the misdiagnosis rate have been as high as 43% that is almost one out of every two people. Controversy often stems from the root of this problem, with awareness rising from cases like Terri Schiavo and Rom Houben. There remains, therefore, a disturbing lack of clinical methodology to assess the functionality of the cerebral cortex, and perhaps most importantly, the cognitive functions that subserve conscious awareness, in behaviourally unresponsive patients.

The most extreme state of behavioural unresponsiveness is coma, a condition that is thought to be caused by a dysfunction of critical brainstem structures that are responsible for producing arousal via ascending, excitatory projections to higher structures of the brain. From coma, patients may progress to a vegetative state (VS). If VS lasts more than 1-3 months, it is considered persistent. In contrast to coma, VS is characterized by intact brainstem functions, and normal sleep-wake cycles. Outward signs of purposeful or voluntary behaviour, however, are not present. Indeed, the presence of weak and inconsistent voluntary behaviour is the crucial distinguishing marker between VS, and another altered state of consciousness, the minimally conscious state (MCS). Making this distinction is a very difficult task for the clinician, who must gauge the subtle differences between reflexive movements and sporadic, weak voluntary actions. Yet another condition, locked-in syndrome (US), can mimic coma. Patients with LIS can be completely aware, yet are profoundly paralyzed, and lack voluntary control not only over their limbs, but also over the tongue, and the muscles that control the palate, jaw, and lower face. Signs of consciousness can sometimes be obtained through voluntary control over opening and closing of the eyes, but some pathologies can result in loss of this capacity, as well as the loss of pupillary reflexes. Under these circumstances, LIS can even mimic brain death.

Currently, there is no standard protocol for assessing VS versus MCS. Given the difficulty and complexity of differential diagnoses between different conditions in patients with an altered level of consciousness, it is not surprising that misdiagnoses are extremely common (close to 50%, as mentioned above). The high rate raises considerable medical, ethical, and legal concerns and places the priority on the need for better diagnosis of conscious awareness. Perhaps equally important is reduction of burden on the individual, their family, and society. While there cases in which little that can be done, once an individual has been properly evaluated as consciously aware it is possible to pursue aggressive intervention through pharmacological treatments, rehabilitation, and compensation training. None of these efforts can reasonably be justified if an individual is deemed as lacking conscious awareness.

Even more serious is the possibility for the termination of life-sustaining therapies. The decision to withhold or withdraw life-support is made by the physician, in conjunction with family members, based on their assessment of the patient's prognosis and level of consciousness. Cases such as that of Terry Schiavo have brought tremendous media attention to the clinical assessment of conscious awareness in behaviourally unresponsive patients. However, the Schiavo case gained public notice only because of the legal battle between Schiavo's mother, and her husband, who had opposite beliefs on whether Schiavo would have wished to live. The termination of life-support is in fact relatively common. In Canada, 10-20% of critically ill patients die in adult intensive care units, and 65-79% of these deaths follow the withdrawal or withholding of treatment. Given that there is increasing pressure on clinicians to terminate treatment or palliative care because of the extreme demand for ICU beds in most clinical settings, it has never been more crucial to develop methods for assessing consciousness that are not subject to the folly of depending on the capacity for behavioural response.

In recent years, there has been increasing interest in the application of functional neuroimaging methods in the assessment of consciousness. Functional neuroimaging methods such as positron emission tomography (PET) and functional MRI provide images of the neuroanatomical pattern of neural activation with good spatial accuracy. PET has been used to demonstrate that MCS patients tend to exhibit more extensive, possibly higher-level cortical processing in response to simple sounds than PVS patients. Several studies have used PET and fMRI to demonstrate residual language processing in VS, often to the subject's own name. Others claim to have demonstrated both language comprehension and volition, as demonstrated by the patient conforming to requests to imagine performing different tasks, such as walking around her house, or playing tennis. Overall, these methods provide promising means to assess conscious awareness in behaviourally unresponsive patients.

Functional MRI measurements, however, are difficult to acquire and analyze in patients with altered conscious awareness, and may not be possible with individuals who are heavily dependent on life-support. Furthermore, routinely assessing consciousness using fMRI would merely place a greater burden on an already overtaxed element of many health-care systems. In Canada, MRI wait times are currently quite long. For example, at Nova Scotia's Capital Health Care hospitals, wait times are about 80 days. In Saskatoon, Saskatchewan, the situation is far worse: a patient may wait as long as 390 days to obtain an MRI scan. Due to this critical MRI shortage, some hospitals are moving towards more strict guidelines for prioritization of MRI use. As such, it would appear unwise to establish fMRI as a primary means of assessing conscious awareness in behaviourally unresponsive patients. While wait times may improve, one thing that may not improve in the foreseeable future relates to the practical limitations of methods like MRI. MRI is large, expensive, and far from being portable. Diagnostic tests like the GCS are so pervasively used and relied on largely due to one feature—they are practical, easy to implement, and the results can be rapidly communicated. While the GCS is often administered in the ambulance and reported to medical professionals prior to or upon arrival, it is unlikely that MRI (and related technologies) will substitute for this assessment in the near future.

In contrast, electroencephalography (EEG) is an established means of examining brain function, and it has arguably the most promise for replacing existing clinical measures like the GCS. EEG is already used as a portable device in the clinic. That is, the barriers to collecting the EEG signals have largely been overcome, but more advanced uses of the technology have yet to be integrated into everyday clinical practice. For instance, measures derived from the EEG called event-related potentials (ERPs) are minute deflections normally buried in the continuous EEG that, over five decades of experimental research, have been tightly linked to discrete stages of processing in the central nervous system. Rather than measuring a correlate of neural activity derived from hemodynamic fluctuations (like fMRI), ERPs measure directly the electrical currents produced by neural activity. Furthermore, ERPs track neural activity in real time, on the order of milliseconds, therefore providing an on-line record of conscious processing (e.g., sensory, perceptual, attentional, memory, and language).

In terms of clinical applications, ERPs have been studied over the last 15 years as an objective, physiological replacement for behavioural-based neuropsychological assessment. This work resulted in a patented method for combining neuropsychological and neurophysiological approaches in aphasia assessment. The work was important foundational evidence for the general concept of decoupling the diagnosis of language function from the limitations of behavioural responses. However, it did not address critical challenges (which require novel solutions):

1) a spectrum of ERP responses exist, which can be integrated into a comprehensive test of conscious awareness. The challenge is to devise an effective method for combining this spectrum of information into a rapid and meaningful clinical test;

2) this test/method cannot be reliant on advanced expertise/training, but rather should be easy to administer, with no prior knowledge/training;

3) it should be possible to run the test on a portable, stable, noise-resistant device that is easily integrated into a wide variety of environments (small, robust, and scalable);

4) the analysis software should be provided with a database of normative subject data for comparison purposes, so as not to rely on any other standardized test or procedure; and 5) the test should produce clinically useful results (which do not require expertise to interpret), and these results should be easily output to current IT communications developments (hand held computer, wireless communications)

Early sensory evoked potentials (EPs) have long been used clinically to assess the integrity of the brainstem in coma. Longer-latency, cognitive ERPs have not yet been integrated into any routine method of clinical assessment. Research, however, has successfully employed cognitive ERPs as a neurophysiological index of mental function under a wide range of clinical conditions that preclude verbal and/or behavioural responsiveness.

For instance, Connolly and colleagues, as disclosed in U.S. Pat. No. 6,993,381 issued Jan. 31, 2006, modified existing neuropsychological tests for use in ERP recording, to perform assessments in dyslexic and aphasic patients, including one young man who suffered from global aphasia and physical disability due to a knife wound to the head. Their ERP measurements indicated that his capacity to understand language was intact, and his subsequent admission to a rehabilitation program resulted in an excellent outcome.

ERPs represent an important alternative to fMRI testing in behaviourally unresponsive patients. However, despite the fact that EEG is relatively inexpensive and can be made portable, particularly when compared to MRI technology, hospitals typically have not provided for the increased demands for EEG monitoring, both in terms of digital EEG machines, or EEG technologist coverage (Young, 2009b). There exists, therefore, considerable need for EEG technology that can be applied by non-experts, and automatically performs clinically useful tests, analyzes data without the assistance of an expert, and produces a clinically meaningful output for health care professionals. Such a device, if made portable and easy use, could not only be used widely in hospitals and clinics but also made available in a range of other settings (ambulances, arenas, nursing homes, home care etc). It could be easily integrated into the Critical Care Cascade—the continuum of care from pre-hospital assistance to ICU discharge and rehabilitation.

A wide variety of ERPs have been used in clinical research to test the functional integrity of sensory and cognitive functions in behaviourally unresponsive patients, including P1, N1, P2, MMN, P300, N400, and P600. In addition, a number of different tests have been proposed for eliciting the higher-level cognitive ERPs, including the patient's own name, non-verbal emotional exclamations, number sequences, and ERP tests based on standardized neuropsychological paper and pencil tests.

Despite the serial stages of processing that are expected to extend from early sensory ERPs to late, cognitive ERPs, it has been repeatedly demonstrated that ERP responses in patients with severely damaged central nervous systems do not necessarily conform to this hierarchy. Lower ERP responses can be lacking, while ERPs to more complex, higher processes are retained. Thus, it is important to utilize a spectrum of ERP tests/component—it is not appropriate to declare a patient cortically non-responsive as a consequence of a negative result for a single ERP.

Hierarchical paradigms also have two other important advantages: they provide a level of consistency when multiple tasks all yield negative results, and they can provide useful information about cognitive specificity when only specific responses are missing.

The following patents have been located in this general field:

U.S. Pat. No. 6,993,381B2—Linking neurophysiological and neuropsychological measures for cognitive function assessment in a patient—Connolly et al.

The above patent describes a method that utilizes audio and visual stimuli to assess language function and memory, as measured by a limited number of ERP components (N400 and P300). The complex procedure and analysis is heavily dependent on user expertise and requires an extended period for data analysis (i.e., it is intended as a neuropsychological assessment method). To that end, this method requires relating components like the N400 to computerized versions of standardized neuropsychological tests. ERP components are statistically assessed using t-tests between pairs of corresponding intervals on the waveforms to the congruent and incongruent terminal words. These intervals have a plurality of widths and are centred on the visually-identified (i.e., user-identified) peak. This method has not been designed for administration as a portable medical test which could be integrated into the Critical Care Cascade. Furthermore, its output requires expert interpretation, and has not been designed for integration with current communications developments (e.g., telecommunications) for rapid and easy communication.

U.S. Pat. No. 6,868,345B1 and WO2004/05441—Monitoring auditory evoked potentials—Jensen—commercial products by Danmeter A/S The above patent describes a method that uses quantitative EEG measures (QEEG) from the spontaneous EEG, as well as middle-latency auditory evoked potentials (MLAEPs) and the electromyogram (EMG) to assess the depth of anaesthesia. The device relies on very specific relationships between these neurophysiological indices and dosages of hypnotic agents. Drug dosage can also be added as an input to the algorithm. The device does not calculate ERR waveforms in a traditional sense.

US2007/0032737A1—Method for assessing brain function and portable automatic brain function assessment apparatus—Causevic & Combs—commercial products by BrainScope The above patent describes a method that assesses both the spontaneous EEG using QEEG, and ERPs to potentially any type of stimuli delivered in potentially any modality. The scoring that is performed by this device is the following: classifies the brain signals as "normal" vs. "alert", if "alert" then goes on to identify whether burst suppression or seizure activity is occurring, if none of these are occurring, it seeks to distinguish organic from non-organic (psychogenic) disorders. These indices are used to assess the neurological state of the patient by providing a single "normal" vs. "abnormal" score, and a diagnosis for an organic/psychiatric disorder. This test is not arranged to provide a standardized assessment of a spectrum of indices of information processing, including sensory and cognitive functions such as perception, attention, memory, and language comprehension. Thus it does not provide a test of conscious awareness.

U.S. Pat. No. 5,540,235—Adaptor for neurophysiological monitoring with a personal computer—Wilson The above patent describes a method for a portable neurophysiological monitoring device that could be used to monitor ECG, EEG, or EMG. The device utilizes wireless connections.

U.S. Pat. No. 5,755,230—Wireless EEG system for effective auditory evoked response—Schmidt et al.

The above patent describes a method for a portable EEG device that communicates with a computer via a wireless connection and delivers verbal stimuli. It is specifically designed for assessing ERPs in response to verbal stimuli in small children, in order to establish whether remedial language instruction is needed. It does not perform a specific, programmed test. It simply provides a means for an experimenter to record verbal stimuli, present them, and record the ERP response.

U.S. Pat. No. 6,052,619, U.S. Pat. No. 6,385,486B1, U.S. Pat. No. 7,471,978, US2009/0076407, and US2009/0227889—Brain function scan system—John or John & John The above documents describe a method for diagnosing brain function using QEEG, evoked potentials (EPs) from stimuli delivered in any modality, and may also utilize infrared or laser sensors to monitor cerebral blood oxygenation. The only functions assessed by EPs in this device are sensory functions, as the EPs elicited are steady-state responses analyzed by FFT. Thus, the device does not extract ERP components or assess any kind of higher-level cognitive functions.

US2009/0312663—System and method for neurometric analysis—John et al.

The above patent describes a method for establishing a server connected to a series of analysis modules which would allow remote users of their device to upload data and analyze it. The functions executed by the local or remote computer (a local computer may download these functions) include: reformatting of the data, automatically edit/remove artifacts, detect epileptiform activity, perform spectral or wavelet analysis of QEEG, transforming numerical indicators to Z-scores, perform discriminant analyses on these scores, perform source localization, and generate a report.

U.S. Pat. No. 6,223,074—Method and computer program product for assessing neurological conditions and treatments using evoked response potentials—Granger The above patent describes a method for assessing whether or not a patient suffers from a neurological or psychiatric condition by performing a variety of ERP tests and comparing the ERP-based measures to data from healthy controls and patients suffering from that disorder. No particular test is pre-established in the program, and it appears that the user should design their own test and collect the healthy control and diagnosed patient data themselves for comparison. The patent particularly covers the extraction of the modified ERP measures, called "vectors" and "projections", and performing a weighted vote based on correlations of those "projections" with ones from healthy subjects and disordered patients. ERP waveforms are not calculated or quantified in the traditional sense.

U.S. Pat. No. 6,317,627 (see also US2002/0082513A1 from Group 2)—Anesthesia monitoring system based on electroencephalographic signals—Ennen et al.—commercial products by Physiometrix The above patent describes a method for a device that uses four "observers" are used to describe patient's state: Beta5 (an EMG index), Patient State Index (PSI) the main index of level of consciousness, Eyeblink, and Suppression (referring to whether burst suppression has recently been observed). This device analyzes spontaneous EEG activity: it does not present stimuli, nor use ERPs. Patient state is determined based on comparison of the QEEG measures with population norms, as well as using data from other states in the same patient. Thus, in terms of EEG measures, the device can only provide a general index of CNS depression. It does not measure any specific neural functions.

U.S. Pat. No. 6,339,721—Brain wave data processing device and storage medium—Yamazaki & Kenmochi The above patent describes a method for using wavelet transformation to extract ERP information from single trial and averaged waveforms. On the averaged waveform, they do use a latency window for finding the ERP component, but then they search within this window using wavelet-based pattern recognition. There is also description of a basic EEG acquisition system. There is no specific test, or specific ERPs measured, it is merely an acquisition system and an automated method for ERP identification.

U.S. Pat. No. 6,493,576—Method and apparatus for measuring stimulus-evoked potentials of the brain—Dankwart-Eder The above patent describes a method to obtain MLAEPs and brainstem auditory evoked potentials (BAEPs), for monitoring anaesthetic depth. The BAEPs are considered a "base" information signal, while the MLAEPs (or potentially other auditory ERPs) are the "variable" signal to track neurophysiological changes. This patent very specifically refers to device use only for anaesthetic monitoring. There is no automated evaluation of the ERPs, just averaging and display.

U.S. Pat. No. 6,832,110—Method for analysis of ongoing and evoked neuro-electrical activity—Sohmer et al.

The above patent describes a method for automatically evaluating ERPs in single trial data. The method can be applied to any ERP.

U.S. Pat. No. 7,373,198—Method and apparatus for the estimation of anesthetic depth using wavelet analysis of the electroencephalogram—Bibian et al.

The above patent describes a method for real-time monitoring of anesthetic depth. Anaesthetic depth is monitored by wavelet transformation of the spontaneous EEG. The description provides for possibilities of using this device to ascertain other states of the brain and well-being of the CNS (a broad-ranging list on p. 12). However, their specific claims state that they are measuring only the "level of depression in the CNS". The method extracts wavelet coefficients from one data set and compares them to either another state in the same individual, or reference data from a group or control. No normative database is provided, the user should obtain "reference data" themselves. Thus, the device does not provide any measure of specific neural functions.

US2003/0199781 Automatic electroencephalogram analysis apparatus and method—Tsuboshita et al.

The above patent describes a method for automatically evaluating the normality/abnormality of the spontaneous EEG using QEEG measures and statistical tests in the form of Mahalanobis distance. The patient's QEEG measures are compared to a reference data set, and Mahalanobis distance is calculated from this reference data set.

US2004/0193068—Methods and apparatus for monitoring consciousness—Burton & Zilberg The above patent describes a method for recording EEG and other physiological measures (ECG, EOG, etc.) using a novel sensor design for the purpose of depth of consciousness assessment. The device may use sleep stage analysis, EEG bispectral analysis, and auditory ERPs. They claim specifically to automatically detect whether the subject is in a transition from a conscious state to a less conscious state, or vice versa. The only auditory ERPs that are mentioned are sensory responses to click stimuli. The resulting BAEPs and MLAEPs are used as a secondary measure to compensate for the very drug agent-specific nature of bispectral (BIS) changes. It tests no specific functions of the brain beyond sensory receptivity, sleep states, and overall CNS depression.

US2008/0167570—Neural event process—Lithgow The above patent describes a method for analyzing either electrocochleogram (ECOG) data or BAEP data using wavelet transformations.

US2008/0255469 and US2009/0177108—Method for monitoring the depth of anesthesia—Shieh et al.

The above patent describes a method for monitoring depth of anaesthesia based on the spontaneous EEG. Recordings are first made on the patient in an alert, awake state. Depth of anaesthesia is then determined by entropy (a type of deviation from the original normal measurement).

US2008/0262371—Method for adaptive complex wavelet based filtering of EEG signals—Causevic The above patent describes a method of filtering and extracting auditory ERPs using complex wavelet transformations which is explicitly applied to BAEPs but may also be used on other ERPs.

U.S. Pat. No. 5,010,891—Cerebral biopotential analysis system and method—Chamoun—commercial products by Aspect Medical Systems The above patent describes a method that claims to assess: depth of anaesthesia, acute cerebral ischemia, level of consciousness, degree of intoxication, and ongoing normal and abnormal cognitive processes. The EEG measures used by this device are QEEG measures extracted from the spontaneous EEG. No stimuli are delivered. Specifically, its indices are third-order autocorrelations or autobispectrum (BIS) performed on either frequency-domain, or parametric values either extracted from single leads, or paired interhemispheric leads. They studied normal individuals, and patients suffering from a range of conditions, and computed what QEEG metrics served best as classifiers for those populations. These metrics are then applied in their device.

Reference is also made to the following papers, the disclosures of which are incorporated herein by reference and to which reference may be made for information to supplement the disclosure hereinafter:

Connolly, J F, D'Arcy, RCN, Newman, R L, Kemps, R. (2000). The application of cognitive event-related brain potentials (ERPs) in language-impaired individuals: Review and case studies. International Journal of Psychophysiology 38: 55-70.

D'Arcy, R C N, Connolly, J F, Service, E, Hawko, C S, Houlihan, M E. (2004). Separating phonological and semantic processing in auditory sentence processing: A high-resolution event-related potential study. Human Brain Mapping 22: 40-51.

Gawryluk, J R, D'Arcy, R C, Connolly, J F, Weaver, D F. (2010). Improving the clinical assessment of consciousness with advances in electrophysiological and neuroimaging techniques. BMC Neurology 10:11.

Kotchoubey, B, Lang, S, Mezger, G, Schmalohr, D, Schneck, M, Semmler, A, et al. (2005). Information processing in severe disorders of consciousness: Vegetative state and minimally conscious state. Clinical Neurophysiology 116: 2441-2453.

Neumann, N, Kotchoubey, B. (2004). Assessment of cognitive functions in severely paralysed and severely brain-damaged patients: Neuropsychological and electrophysiological methods. Brain Research. Brain Research Protocols 14: 25-36.

Ponton, C W, Don, M, Eggermont, J J, Kwong, B. (1997). Integrated mismatch negativity ($MMN_i$): A noise-free representation of evoked responses allowing single-point distribution-free statistical tests. Electroencephalography and Clinical Neurophysiology: 143-150.

Rodriguez-Formells, A, Schmitt, B M, Kutas, M, Münte, T F. (2002). Electrophysiological estimates of the time course of semantic and phonological encoding during listening and naming. Neuropsychologia 40: 778-787; and Sculthorpe, L D, Campbell, K B. (2011). Evidence that the mismatch negativity to pattern violations does not vary with deviant probability. Clinical Neurophysiology, DOI: 10.1016/j.clinph.2011.04.018

Sinkkonen, J, Tervaniemi, M. (2000). Towards optimal recording and analysis of the mismatch negativity. Audiology & Neuro-otology 5: 235-246.

Vanhaudenhuyse, A, Laureys, S, Perrin, F. (2008). Cognitive event-related potentials in comatose and post-comatose states. Neurocritical Care 8: 262-270.

SUMMARY OF THE INVENTION

It is one object of the invention to provide a comprehensive test of conscious awareness that tests a spectrum of ERP responses rapidly, and produces clinically meaningful output. This clinically meaningful output can be established by comparing the test output to a pre-programmed normative database. This test/method is preferably not reliant on advanced training, and is easy to administer with no prior knowledge or training. The output of this test can be easily communicated via integration with current IT solutions, such as wireless communications.

According to one aspect of the invention there is provided a method for analysis of the extent of conscious awareness and/or likelihood of recovery of a patient comprising:

applying to the patient a sensory stimulus sequence generated by a stimulator;

while applying the stimulus sequence, carrying out an EEG or MEG on the patient to record waveform signals from an array of sensors on, in, or near the head of the patient;

using software provided in a processor to process the waveform signals in order to locate waveform peaks, identify the evoked responses contained in the waveform and obtain quantitative measures of these evoked responses;

and using the software to generate and communicate scores based on the quantitative measures that are indicative of the extent of conscious awareness and/or likelihood of recovery of the patient.

Preferably the stimulus sequence is a compressed stimulus sequence that elicits a plurality of evoked responses in a time less than 5 minutes.

Preferably the stimulus sequence is automated and only requires user input related to patient-identifying information.

Preferably data processing by the software is automated with no user input required.

Preferably the software carries out waveform peak detection, the evoked responses identification, and quantitative measurement of the evoked responses of interest automatically with no input from the user.

Preferably the quantitative measures of the patient's evoked responses are automatically compared to normative values from a database.

Preferably the method includes entering demographic information to improve the specificity of the normative database comparison.

Preferably the patient's results, comprised of evoked response features and scores, are compared to one or more of the patient's own results from previous assessments.

Preferably the evoked responses are subject to validity and reliability checks that are summarized in validity and reliability scores.

Preferably the sensory stimulus sequence elicits evoked responses related to a plurality of brain functions.

Preferably the brain functions are comprised of sensory processing, perceptual processing, attention/alerting mechanisms, memory retrieval, and language processing.

Preferably the brain functions are selected from the group consisting of: sensory processing, perceptual processing, attention/alerting mechanisms, memory retrieval, and language processing.

Preferably the evoked responses related to sensory processing are comprised of obligatory sensory evoked responses.

Preferably the evoked responses related to perceptual processing are comprised of evoked responses that signal the detection of changes in the stimulus sequence.

Preferably the evoked responses related to attention/alerting mechanisms are comprised of evoked responses that signal attention switching and memory allocation to the presented stimulus.

Preferably the evoked responses related to memory retrieval are comprised of evoked responses that signal memory-based detection of salient stimulus features.

Preferably the evoked responses related to language processing are comprised of evoked responses that signal detection that a verbal stimulus violates linguistic expectancies.

Preferably the stimulus sequence is comprised of verbal and nonverbal stimuli.

Preferably the arrangement of nonverbal stimuli is complex and elicits evoked responses related to sensory processing, perceptual processing, and attention/alerting mechanisms.

Preferably the nonverbal stimuli are comprised of spectrally rich, musical sounds. Such nonverbal stimuli can include a series of rapidly-presented sounds that generally follow one or more standard rules or regularities. Such nonverbal stimuli can include violating sounds which elicit evoked responses that are related to perceptual processing. Such nonverbal stimuli can include a plurality of rule-violating sounds, and the software averages some of these different rule violations together to increase the number of epochs included in the averaged waveform used to derive the perceptual evoked response without increasing testing time. Such nonverbal stimuli can include sounds with a changed feature to elicit the attention-based evoked response, wherein the other features of the sound are consistent with the standard rules or regularities of the sequence.

Preferably the verbal stimuli include personal identifiers comprised of a name of the patient, a control name, and personal pronouns. Alternatively the verbal stimuli can include words or groups of words that build linguistic expectancy or violate linguistic expectancy.

Preferably the software comprises a peak localization algorithm, an evoked response identification algorithm, an evoked response quantification algorithm, and a score generation algorithm.

Preferably the evoked response localization algorithm utilizes a calculus derivative method, which performs mathematical decomposition of the averaged waveform by determining the zero crossings of the waveform's first and second derivatives, yielding candidate peaks and inflection points of the waveform's curvature, and guards against noise-based deflections by comparison to single-trial data.

Preferably, if several candidate peaks have been identified, small peaks riding on top of larger deflections are rejected by amplitude thresholding.

Preferably the evoked response identification algorithm determines whether a candidate peak is an evoked response based on identification criteria selected from the group consisting of experimental condition, polarity, latency, and scalp distribution.

Preferably the evoked response identification algorithm further comprises an adaptive pattern recognition process for cases in which the identification criteria do not identify an evoked response.

Preferably the evoked response quantification algorithm calculates quantitative measures of evoked response features comprising peak latency and peak amplitude by inferred baseline and peak to peak measures.

Preferably the software generates scores comprising a diagnostic score, a reliability score, a validity score, and a prognostic score.

Preferably points in the diagnostic score are allotted based on evoked responses related to a plurality of brain functions.

Preferably points in the diagnostic score are allotted based on the statistical assessment of differences between quantitative measures of the patient's evoked responses and normative values from a database.

Preferably points in the reliability and validity scores are allotted based on the repeatability and/or consistency of the waveforms which contain the evoked responses.

Preferably points in the prognostic score are allotted based on the statistical relationships between averaged waveform features and historical outcomes of patients diagnosed with the same condition.

The invention shown and described herein can also relate to the apparatus which is adapted and arranged to carry out the specific method steps set forth above.

BRIEF DESCRIPTION OF THE DRAWINGS

One embodiment of the invention will now be described in conjunction with the accompanying drawings in which.

DETAILED DESCRIPTION

Figure 1:
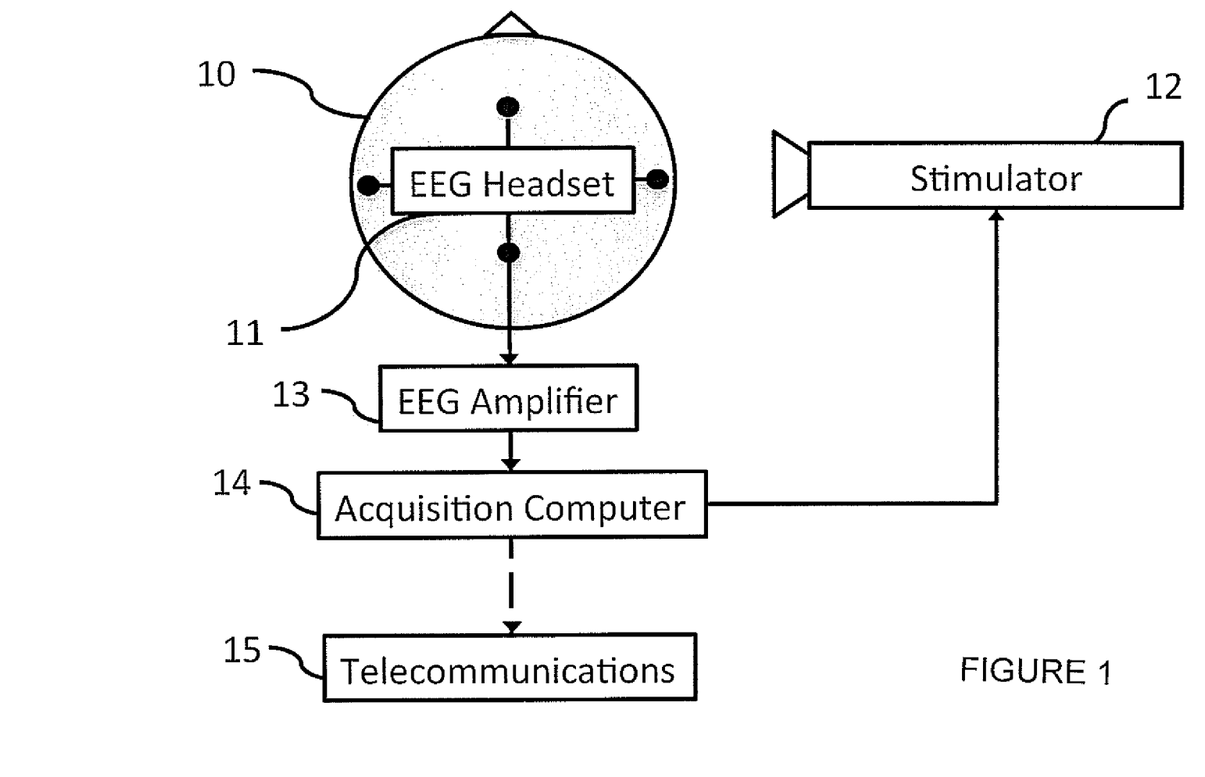
FIG. 1 is a schematic illustration of the preferred embodiment of the EEG acquisition device.

FIG. 1 shows an apparatus for the method described herein and includes a patient 10 connected to an array of EEG electrodes 11 and arranged to receive sensory stimulation from a stimulator 12. The electrodes receives signals from the brain which are transmitted to an EEG amplifier 13, and then an acquisition computer (processor) 14, which communicates to the physician through a telecommunications program 15. The computer also provides controls the stimulator 12.

Figure 2:
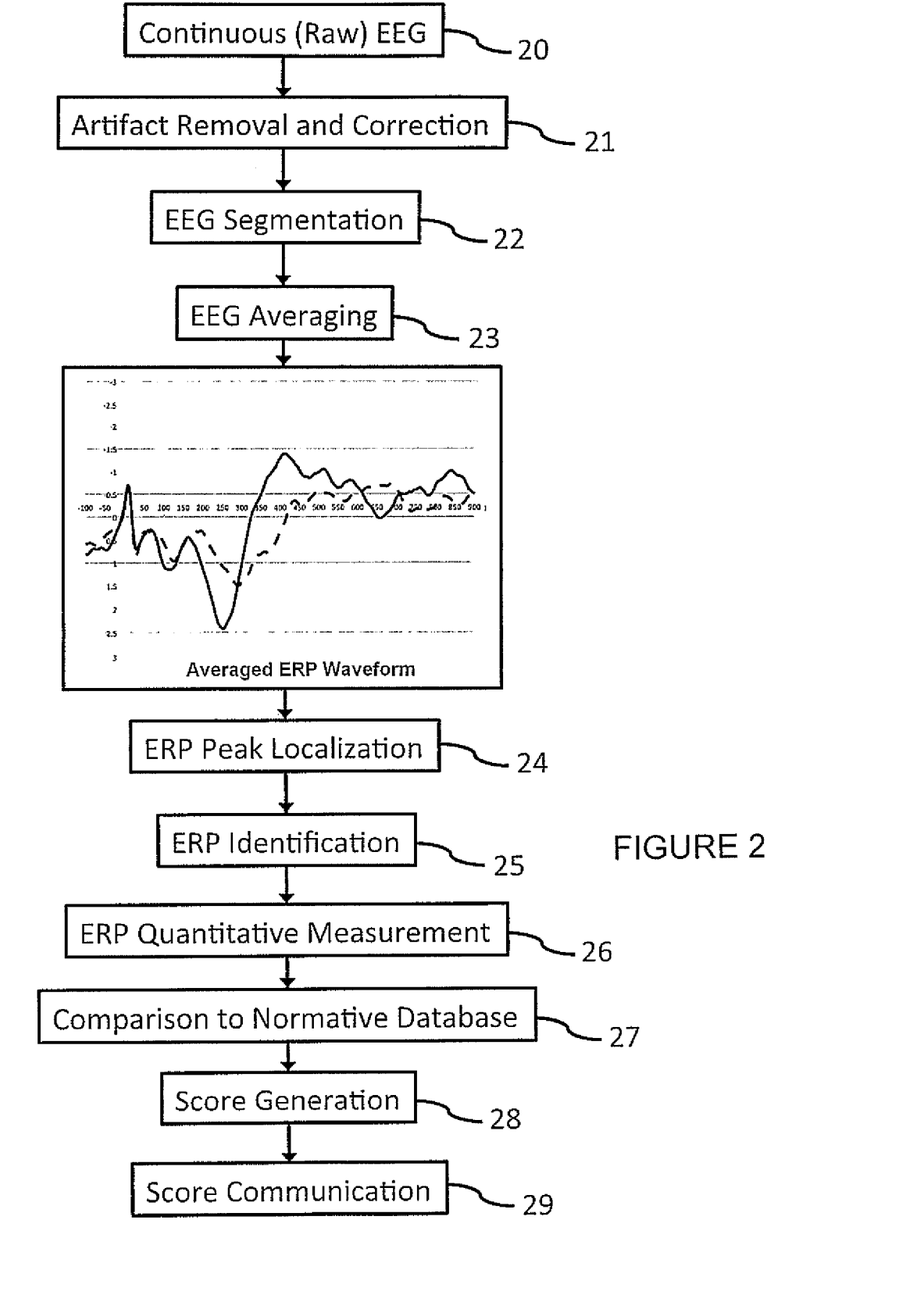
FIG. 2 is an illustration of the processing steps beginning at the continuous, raw EEG data and terminating at the output of a clinically meaningful score.

In FIG. 2 is shown schematically an embodiment of the method which is set out in a flow chart which includes the following steps:

Step 20—Continuous (Raw) EEG Data
Step 21—Artifact Removal and Correction (e.g. baseline correction, EOG correction)
Step 22—EEG Segmentation
Step 23—EEG Averaging
Step 24—ERP Peak Localization (CD Method)
Step 25—ERP Component Identification (based on identification criteria, and/or the adaptive pattern recognition process)
Step 26—ERP Component Quantification (e.g., IB and PP amplitude measurement)
Step 27—Comparison to Normative Database (e.g. amplitude ranks, percentile ranks, z-scores)
Step 28—Score Generation (Dx, Rx, Vx, Px)
Step 29—Score Communication (e.g. device screen output, short report, long report)

The embodiment of the method described hereinafter as shown in FIGS. 1 and 2 therefore provides a stimulus sequence that produces 5 different indications of normal cortical processing, in the form of evoked responses. Normal cortical processing is important for conscious awareness. Therefore, for the purpose of this device, conscious awareness is operationally defined as the general integrity of brain function. Given that it is impractical to test all brain functions, a group of key indicators across a spectrum of brain functions should be selected to indicate general brain functionality. The current embodiment of this method tests a group of brain functions comprising sensory processing, perceptual processing, attention/alerting mechanisms, memory retrieval, and language processing. Other brain functions, such as motor preparation, stimulus expectancy, or selective attention, among others, could conceivably be tested to achieve the same goal, and remain within the spirit and scope of the invention.

In order to test the functionality of the brain, stimuli must generally be presented. These stimuli are presented as a sensory stimulus sequence, via one or more stimulators (e.g., speakers or earphones for auditory stimuli, or a computer monitor for visual stimuli). If registered and processed by the brain, each of the stimuli in the stimulus sequence elicits an evoked response. Evoked responses comprise a variety of brain responses such as event-related potentials (ERPs), event-related fields (ERFs), event-related synchronization (ERS) and event-related desynchronization (ERD). Although any type of evoked response could be used in this method, the current embodiment is described using ERPs. Evoked responses are derived from either electroencephalographic (EEG) or magnetoencephalographic (MEG) recordings that are collected concurrently with presentation of the stimulus sequence. These recordings are made from an array of sensors (in EEG, these are electrodes; in MEG they are superconducting quantum interference devices) that are placed on, in, or near the patient's head. Brain functionality could be tested using stimuli in substantially all modalities. Although auditory stimuli are utilized in an embodiment of the invention as described, the presentation of stimuli in other sensory modalities can be used.

Sensory Processing: In humans, the onset of any relatively abrupt sound elicits a series of known ERP components. These ERP components signal auditory processing all the way from the brainstem to the auditory cortex. ERPs that occur consistently to the onset of any sound are called "obligatory" sensory evoked responses. At the level of the brainstem, these include brainstem auditory evoked potentials (BAEPs), and at the level of the thalamus and early auditory cortex, middle-latency responses (MLRs) occur. Later processing in the cortex is indexed by a series of ERP components called the P1-N1-P2 complex. When computerized averaging became available in the early 1960s, the P1-N1-P2 complex began to be used in objective audiometry to estimate hearing sensitivity. The P1, N1, and P2 all index neural encoding of sound at the level of the auditory cortex.

Clinical research has often relied on the N1 to demonstrate sensory function in non-communicative patients. The averaged waveform to sounds in children is dominated by P1, and P1 is the only component of the adult P1-N1-P2 complex that is resistant to rapid rates of presentation. Objective tests for auditory function often also rely on BAEPs, MLRs, and can often use very fast rates of presentation, with which these ERPs can summate in so-called "steady-state" responses. The evoked responses of interest for sensory processing in the preferred embodiment are P1 and N1, but other parts of the obligatory sensory response, like BAEPs, MLRs, and steady-state responses remain of interest.

Perceptual Processing: When the auditory cortex processes incoming sounds, the acoustic and temporal features of the sounds are organized into perceptually meaningful auditory objects, groups, and streams. In general, two types of ERPs are used to probe how the brain organizes sounds: the responses to standard (repeated) stimuli that are related to the encoding of the regularities of the sequence, and responses to deviant (changed) stimuli that are related to the detection of changes in the stimulus sequence. Among the former ERPs are the N1 and repetition negativity (RN). Among the latter are the N2 family of components, such as the N2a and/or MMN, N2b, and the object-related negativity (ORN).

A common ERP that is used to study perception is the MMN. The auditory MMN occurs when the brain detects that an incoming sound violates regularities that it extracted from the recent acoustic past. The MMN has long been considered to be the ERP that is most closely tied to auditory sensory memory, which forms the basis of conscious perception. Indeed, the amplitude of the MMN varies with the perceptibility of "deviant", regularity-violating stimuli. The MMN has a large number of clinical uses, and has proved to be particularly advantageous in the assessment of coma. More than any other ERP component, the presence of an MMN in coma is predictive of a positive outcome. Its presence is also strongly predictive of positive outcome in PVS and MCS. The evoked response of interest for perceptual processing in the preferred embodiment is the MMN, however other ERPs that are tied to perception, such as the N1, RN, and other members of the N2 family of components remain of interest.

Attention/Alerting Mechanisms: The P300 has been described as the best candidate ERP for the role of "correlate of conscious awareness". It is typically obtained in an active "oddball" paradigm, in which a homogeneous series of identical stimuli is broken at rare and unpredictable times by a physically changed deviant that is designated as a target. The P300 actually represents the overlapping of ERP subcomponents, particularly P3a, an index of attention-switching that can be observed even if stimuli are not attended, and the P3b, which generally only occurs if deviant stimuli are designated as targets for active detection. The P3b is thought to index memory allocation—specifically, an update of working memory representations. The P300 tends to occur to unpredictable biologically or personally relevant stimuli. Like the MMN, it is useful in predicting survival in coma. There is an enduring debate in basic P300 research concerning whether the P300s evoked by different types of stimuli (e.g., "novel" environmental sounds versus task-specified targets) indeed evoke the same response. The evoked response of interest for attention/alerting mechanisms in the preferred embodiment is the P300 response to loud intensity violations, but other varieties of P300 responses, including the P3a evoked without the later P3b, remain of interest.

Memory Retrieval: Since the occurrence of the P300 depends on both biological and personal relevance (or "salience"), it can be used to gauge whether highly-learned information has been recognized by access to long-term memory. One highly-learned piece of information with strong personal relevance is a person's own name. In healthy subjects, presentation of an individual's own name reliably evokes a P300, even during sleep. However, memory access occurs earlier than the P300, and can be indexed by ERPs in the N2 family (e.g., N2, MMN, N2b). The evoked responses of interest for memory retrieval in the preferred embodiment are N2 and P300, although other memory-related ERPs remain of interest.

Language Processing: Linguistic processing in the human brain is accompanied by a number of ERPs that index different aspects of language. Any word or group of words builds a linguistic expectancy for the words that should follow, based on the structural rules that are inherent to any language. Language-related ERPs are generally elicited by words that violate a linguistic expectation that was built up by previously presented words. Such ERPs include, for example, the phonetic mismatch negativity (PMN), the N400, the early language associated negativity (ELAN), the late positive component (LPC), and/or the P600. Language processing in the present embodiment is assessed based on semantic processing. The brain exhibits a different neural response to semantically related words than semantically unrelated words. This differential response manifests at the level of the N400, a negative component with a central-parietal topography that peaks approximately 400 ms from word onset. When semantic expectations are built by presenting either a single word "prime", or an entire sentence, the N400 is larger to semantically incongruent than congruent words. For example, the semantic expectations built by the phrase, "She likes her coffee with cream and _" would result in a small N400 for the terminal word "sugar", but a large N400 for the terminal word "socks". The best predictor of N400 amplitude is a word's predictability, with less predictable words eliciting a larger N400. The presence of an N400 for patients in PVS or MCS tends to predict a better outcome, and has been used successfully as a basis for rehabilitation in an aphasic and physically disabled patient. The evoked response of interest for language processing in the preferred embodiment is the N400, but other ERPs related to linguistic processing, such as the PMN, ELAN and LPC remain of interest.

There are a number of challenges that have long faced those who wish to apply ERPs in clinical research. First, and perhaps most challenging, is the length of time required for testing. The extraction of ERPs from the continuous EEG typically requires long recording times. ERPs have fairly small amplitudes in comparison to the background EEG and environmental electromagnetic noise, and are derived by presenting stimuli many times. The continuous EEG is then segmented into epochs (single trials) that are time-locked to stimulus onset. When these epochs are averaged together, the background EEG, which is essentially random with respect to the stimulus, averages towards zero, while the deflections that reflect processing of the stimulus are retained. An essential concept in this signal averaging method is the signal to noise ratio. The smaller the desired signal (the ERP) is compared to the noise (the background EEG and environmental noise), the more epochs are necessary to remove the background noise to a point at which the signal can be distinguished. Therefore, for small ERP components, such as the MMN, long testing times are typically required.

Long testing times, however, are often not available in real-world clinical settings. Pre-hospital scenarios, such as ambulance transportation, require that testing time be kept to a minimum. Even in the ICU, testing times should be kept short. For instance, patients who are in a vegetative state have limited time for testing due to their many therapeutic and rehabilitation procedures. Long testing times also invite a number of unwanted influences on the ERP response, including habituation, fluctuations in arousal, fatigue, and latency jitter, all of which may cause erroneous negative results.

The method therefore uses a compressed stimulus sequence that maximizes the number of usable trials for deriving ERPs (or their magnetic counterparts, event-related fields, ERFs) while minimizing recording time. One way to maximize the number of trials used for deriving ERPs while minimizing recording time is to present stimuli rapidly (e.g., at a rate higher than 1 Hz). In order also to minimize the influence of attention or arousal changes that may occur as a consequence of injury, we have selected stimuli that have been demonstrated to elicit the desired ERP waveforms even during sleep in healthy subjects. This method can be applied for different stimulus types and different sensory modalities (auditory and visual). An example of the method for the auditory modality is provided below:

The auditory consists of verbal and nonverbal parts. The nonverbal sequence consists of a pattern of sounds composed of rapidly-presented tones, which preferably are spectrally rich. Spectral complexity enhances the MMN response. The spectrally complex tones in the sequence include, but are not limited to, harmonics, chords and instrument sounds. These spectrally complex tones are preferably delivered in a sequence that contains one or more rules or regularities. This comprises the standard sequence. The "standard" rules or regularities of the sequence are features of the stimulus sequence that remain unchanged for the majority of stimuli. For instance, in the preferred embodiment, the standard sequence consists of two types of tones, A and B, which alternate (e.g., ABABABAB . . . ). Some examples of standard rules or regularities in this sequence might be "A follows B", "B follows A", or even "every second tone is B". Tones that violate the rule(s) of the standard sequence elicit an MMN in addition to the obligatory sensory ERP components. The MMN elicited by rule violations is quite resistant to fluctuations in attention, occurs during sleep, and is relatively unaffected by presenting large numbers of rule violations in a short amount of time. By inserting different types of rule violations into this sequence, and averaging these different deviants together, we are able to increase the number of epochs included in the averaged waveform used to derive the MMN, without increasing testing time.

Both the MMN and P300 occur to deviant stimuli, but they are typically obtained in different auditory sequences for several reasons. Under "active" conditions, in which the subject is required to attend to the sequence and detect deviant sounds, the MMN is overlapped by another component called the N2b. However, elicitation of the full P300 typically only occurs under active task conditions: under the "passive", non-attend conditions used for MMN elicitation, usually only the P3a occurs. The P3a constitutes the first part of the full P300 response, indicating an attention switch, but not the memory allocation that is signalled by the later P3b. Furthermore, while many epochs are required to reveal the small-amplitude MMN, thus requiring that deviants be presented fairly often to reduce testing time, the relatively large P300 requires few epochs, but these deviants should be relatively widely spaced in time. For this reason, most research studying the MMN and P300 in the same patient evokes them using separate stimulus sequences. Our novel compressed stimulus sequence elicits both the MMN and the P300 in a single 2.5 minute sequence.

Increased loudness, or intensity, represents the only type of physical deviance that can elicit a full P300 response (i.e., both P3a and P3b) under passive conditions. Therefore, in addition to the variety of rule deviants that are used to elicit the MMN, the tonal sequence also contains very infrequent deviants of increased loudness to elicit the P300. Deviants of increased loudness can be used to elicit the P300 even during sleep. Importantly, the P300-eliciting intensity deviants in the tonal sequence possess the appropriate pitch, duration, and serial position to conform to the standard auditory pattern. As such, they reinforce the auditory pattern, which allows MMN-eliciting rule violations to be presented relatively soon following intensity deviants. This allows us to keep testing time extremely short.

The verbal portion of the auditory sequence contains words spoken by recorded and synthesized voices. In sleep research, incongruent words in single word priming, tend to produce a smaller N400s than incongruent words at the end of sentences. Therefore, the preferred embodiment of the verbal sequence consists of sentences. These sentences have been optimized for brevity and their degree of contextual constraint. The amplitude of the N400 is most related to word predictability, known as the Cloze probability. Glaze probability is determined by surveys, by providing sentences with no terminal words and having respondents fill in the word that they expect most naturally ends the sentence. We selected sentences that constrained the terminal word to a single terminal word in at least 80% of respondents (i.e., sentences with a minimum 80% Cloze probability). The expected terminal word was the "congruent" word for ERP averaging, and these terminal words were redistributed among the sentences for the "incongruent" condition. To minimize test duration, each of these sentences, including terminal words, were restricted to 10 syllables or less.

If name stimuli are presented alone, they should be preceded and followed by silent periods. Integrating the name stimuli into the sentences, therefore, helps to minimize the time required for verbal stimulus presentation. The first words of the sentences (the grammatical subjects of the phrases), therefore, are proper names. In the preferred embodiment, half of the sentences begin with the patient's own name, and half of the sentences begin with a different, control name that neither sounds like the patient's name, nor is an alternate version of the patient's name (e.g., if a patient's name is Michael, the other name would not be Mike or Buck). Under circumstances where the names of the patient's loved ones are known, these may also be excluded from presentation as the control name. The patient's own name should demonstrate a large P300 versus the control name. In our experience, the N2 ERP often differentiates the patient's own name from the control name as well. To allow for circumstances in which the patient's name is not known, the method also has the option of beginning half of the sentences with "he", and the other half with "she". In this case, the evoked responses related to memory processing are not obtained. The approximate testing time for the verbal sequence is approximately 2.5 minutes, with this duration dependent on the length of the names utilized.

Together, this novel auditory tone and verbal stimulus sequence allows us to extract P1-N1, MMN, P300s related to both biological and personal relevance, and the N400 (or their magnetic counterparts), in approximately 5 minutes. The exact duration of the stimulus sequence, of course, depends on the length of the patient's own name, and the control name that is selected for presentation.

It is important to note that normally, the stimulus sequences used for eliciting evoked responses must be designed and programmed by the user. In this method, the stimulus sequence is pre-programmed, and presented automatically by a processor. User input is only required to provide identifying information about the patient, such as their name, and if desired, exclude the names of the patient's close family and friends from selection as a control name.

Waveform Analysis Software

ERP analysis is a very specific technique that is rarely taught to EEG technologists and health care professionals. As such, the smooth integration of ERP-based assessment techniques into most health care systems requires software that is capable of extracting and quantifying ERPs in an automated fashion.

As shown in FIG. 2, the continuous raw EEG data 20 from the EEG amplifier 13 is processed in the series of steps set out above.

Pre-processing steps 21, 22, and 23 provide correction for eye movement artifact, artifact rejection, continuous EEG segmentation, and averaging, which are typical to ERP analysis, and are commonly performed in a semi-automated fashion with relatively little user input.

However, ERP components are typically identified by visual inspection of the averaged waveform. Quantitative measures, such as amplitude and peak latency, are then extracted based on user-identified values. For instance, upon visual inspection of the waveform to an incongruent word, a user may quantify the N400 as the average amplitude within a 40 ms window surrounding the visually-identified peak. To eliminate the need for user input from an ERP expert, and shown schematically at steps 24 and 25 the software described herein includes pattern recognition software that automatically identifies ERP components (or in the case of MEG recording, event-related field, ERF components) in the averaged waveform, and obtains quantitative measures of those components.

Generally, ERP components are identified based on 6 features: experimental condition, polarity, latency, duration, morphology, and scalp topography. However, severe brain injury can change many of the features of ERP components. The expert-defined rules, therefore, mainly rely on the most fundamental characteristics of ERP components: experimental condition, polarity, and latency. The remaining features are integrated to augment the algorithm wherever possible.

The software performs at least the following tasks: 1) peak localization, 2) evoked response identification, 3) evoked response quantification, and 4) score generation. These tasks are functionally distinct, but may be executed together or in parallel in the actual algorithm.

1) The software was developed using 3 peak localization methods: a confidence interval (CI) method, an integrated waveform method (IW), and a calculus derivative method (CD). Of these 3 methods, the CD method yields the best results with the relatively noisy data that results from using a short testing time. Therefore the current embodiment of the device relies primarily on the CD method, though the CI and IW methods remain of interest. Different peaks should be sought for different types of evoked responses. In the case of ERPs and ERFs, peaks are sought in a waveform that describes a time course of voltage values. In ERS and ERD, peaks are instead sought in spectrograms or a time course of spectral changes (known as a time-frequency response plot).

The first peak localization method is a novel confidence-interval (CI) based method that uses statistical means to avoid noise quantification. Rodriguez-Formells, 2002, (referred to above) describe a similar method, involving t-tests that are performed on waveforms from a group, rather than data from a single individual. The algorithm calculates the mean amplitude and confidence intervals within a window of predetermined duration. In an embodiment, the window duration is 40 ms. The algorithm then slides this window forward in time by a prescribed distance, in an embodiment, 4 ms, with each iteration. If a plurality of consecutive sliding windows do not span zero, the latency of the first sliding window is considered to be the onset of a peak. In an embodiment, 4 consecutive windows that do not span zero are required to establish peak onset. Following this onset point, the latency of the first of a plurality of consecutive sliding windows that do span zero is considered to be the offset of a peak. Again, in an embodiment, 4 consecutive windows are required to establish peak offset.

However, when testing times are short, and thus the number of samples is small, statistical tests may fail to find significance even when an ERP component really is present. This situation is exacerbated by the presence of environmental electrical noise. Thus, the algorithm also uses a non-statistical peak localization method called an integrated waveform (LW). This method was first described by Ponton and colleagues (referred to above) for use in identifying and quantifying the MM. In the averaged waveform, small peaks produced by random noise are locally offset by neighbouring troughs. In the IW, the cancellation of adjacent noise-derived deflections results in a plateau, while the onset of a peak is the point at which successive voltage values begin to summate in one direction or another. The offset of the peak is defined by the point at which successive data points cease to summate in that direction, resulting in a plateau.

A sufficiently noisy waveform, however, will contain enough noise that both the CI method and the IW method will fail to identify a significant peak. Indeed, this is often the case with short recording times. Therefore, the preferred method for peak localization in the present embodiment of the method is the calculus derivative (CD) method. The CD method performs a mathematical decomposition of the averaged waveform by determining the zero crossings of the waveform's first and second derivatives, yielding peak and inflection points of the waveform's curvature. Since even very small peaks that are indeed noise riding on top of a larger, true ERP component can be identified using this method, it also employs an amplitude thresholding method whereby small peaks are rejected from further analysis. Specifically, if a small peak does not reach a certain percentage of the larger peak's amplitude, it is rejected.

2) Once peaks have been localized, they must be identified as evoked responses. First, identification criteria are applied that describe generic ERP component characteristics based on several basic features, such as experimental condition, latency, and polarity. Scalp distributions are also examined when needed. Appropriate peaks that fit these criteria are selected as ERP components.

However, since these identification criteria were established based on the existing experimental literature, which primarily deals with group averages of many individuals, individual waveforms often do not conform easily to these rules. For instance, the identification criteria for the N400 for incongruent terminal word may be that it occurs within the 300 ms to 500 ms post-stimulus window, and is a relatively large negative peak compared to its surrounding peaks. However, a particular person's N400 may manifest itself outside this search window, and be of smaller negative amplitude relative to its surrounding peaks. Its selection depends not only on the identification criteria of amplitude and latency, but also on the peak's shape and curvature, its relationship to peaks in other waveforms for different experimental conditions (in this case, the congruent terminal word), and the shape and curvature of the waveform between this peak and its neighboring peaks. These are all subtleties in waveform morphology that a human ERP expert takes into consideration in selecting an ERP component.

In order to capture as much as possible the nuances of a human ERP expert's decision-making process, the algorithm also undergoes a secondary adaptive pattern recognition process. In part, this adaptive pattern recognition process performs a series of automated and iterative adjustments to the previously-described identification criteria to accommodate, where possible, the differences between individuals. The adaptive pattern recognition process also uses other criteria that are introduced as-needed to examine subtle, qualitative features of an evoked response. This enables the algorithm to assess not only features that are included in the classical definitions of evoked responses such as amplitude, latency, and polarity (which are encompassed by the identification criteria), but also to examine a particular peak's shape and curvature. Relationships with peaks in waveforms for different experimental conditions are also examined, such as relative amplitudes and crossover points between the waveforms. Because the inherent variability of the individual waveforms prohibits the universal applicability of any one set of rules as selection criteria, the algorithm has built-in flexibility to adjust search criteria when needed, and is therefore sufficiently versatile to accommodate differences in component characteristics between individuals. This procedure emulates the pattern recognition rules that are used by evoked response experts, and maximizes the likelihood of evoked response identification.

A potential improvement upon this method is the implementation of machine learning, rather than human-defined rules, to develop the algorithms for peak detection and identification. This could be achieved by presenting a machine learning algorithm with many examples of evoked responses (e.g., waveforms containing a P300 response) from different individuals. Machine learning algorithms use examples of user-classified stimuli to derive their own rules for pattern recognition. These rules would then be implemented as the peak localization and identification stages of the method. While machine learning is not implemented in the current embodiment, it remains within the spirit and scope of the invention.

3) Once evoked responses have been identified, they must be quantified as shown in step 26. Common quantitative measure for ERPs include, but are not limited to, onset latency, offset latency, peak latency, peak amplitude, mean amplitude, and area. Different types of quantitative measures are required for different types of evoked responses. For instance, ERS and ERD require measures of spectral power. A preferred embodiment quantifies ERP components in terms of peak latency and amplitude. Peak amplitude is measured in two ways. One is a peak to peak measure of the maximum voltage difference between the peak of interest and the two surrounding peaks of different polarity. The other is a novel method in which an "inferred baseline" is calculated as the average voltage of the two surrounding peaks of different polarity. Peak amplitude is then measured as the voltage difference between that average and the peak of interest.

The Score Calculation

There is much interest in the use of ERPs (and by extension, their magnetic counterparts) as a part of standard testing procedures in non-communicative patients. However, the tools used in ERP assessments, to date, remain in the research domain: there is little normative data upon which clinical assessments could be made. Like any medical or psychometric test (e.g., blood pressure, IQ), ERPs have little diagnostic meaning unless they are compared to the normal population. Indeed, the adaptation of existing standardized psychometric tests for ERP elicitation has proven extremely useful for assessing patients who have lost the capacity for verbal communication.

When formulating a new test on the basis of ERPs, however, it should be taken into account that ERPs vary drastically with a number of parameters, including in the composition of the stimulus sequence, level of consciousness at the time of testing, and the equipment used for EEG recording and analysis. Therefore, ERP amplitudes in patients cannot be directly compared to the amplitudes that have been reported in the experimental literature for either diagnostic or prognostic purposes. ERP testing should be performed, as shown in step 27, with reference to a normative sample collected specifically for clinical use. In order to collect this normative data, many aspects of the testing procedure, including the length of the experiment, measurement equipment, and the quantification process should be carefully standardized. In other words, changing almost any single aspect of the hardware, software, or stimulus sequence that is used for ERP testing requires the collection of an entirely new normative sample. As shown in Step 28, we have developed a method for producing clinically relevant scores based on ERP measures, or their magnetic counterparts, compared to values from a normative database that conforms to these requirements.

In the present embodiment, the test yields 5 indicators of conscious awareness: sensory processing, perceptual processing, attention/alerting mechanisms, memory retrieval, and language processing. Each of the indicators can generate up to 4 scores: 1) Diagnostic score (Dx): a multipoint score that reflects cognitive function, as revealed by ERP indicators across the spectrum of information processing; 2) Reliability score (Rx): a multipoint reliability check evaluating the occurrence of repeatable components; 3) Validity score (Vx): a multipoint validity check evaluating the "fit-to-template" of components (e.g., morphology); and 4) Prognostic score (Px); a multipoint score based on the statistical relationships between ERP waveform features and patient outcomes.

The brain functions that are included in the Dx score are sensory processing, perceptual organization, attention/alerting mechanisms, memory retrieval, and language processing. These functions are reflected by P1-N1, MMN, P300 (to tones), N2 and P300 (to names), and N400 ERP components, respectively. The scores apply equally to the magnetic counterparts of these ERPs.

Figure 3:
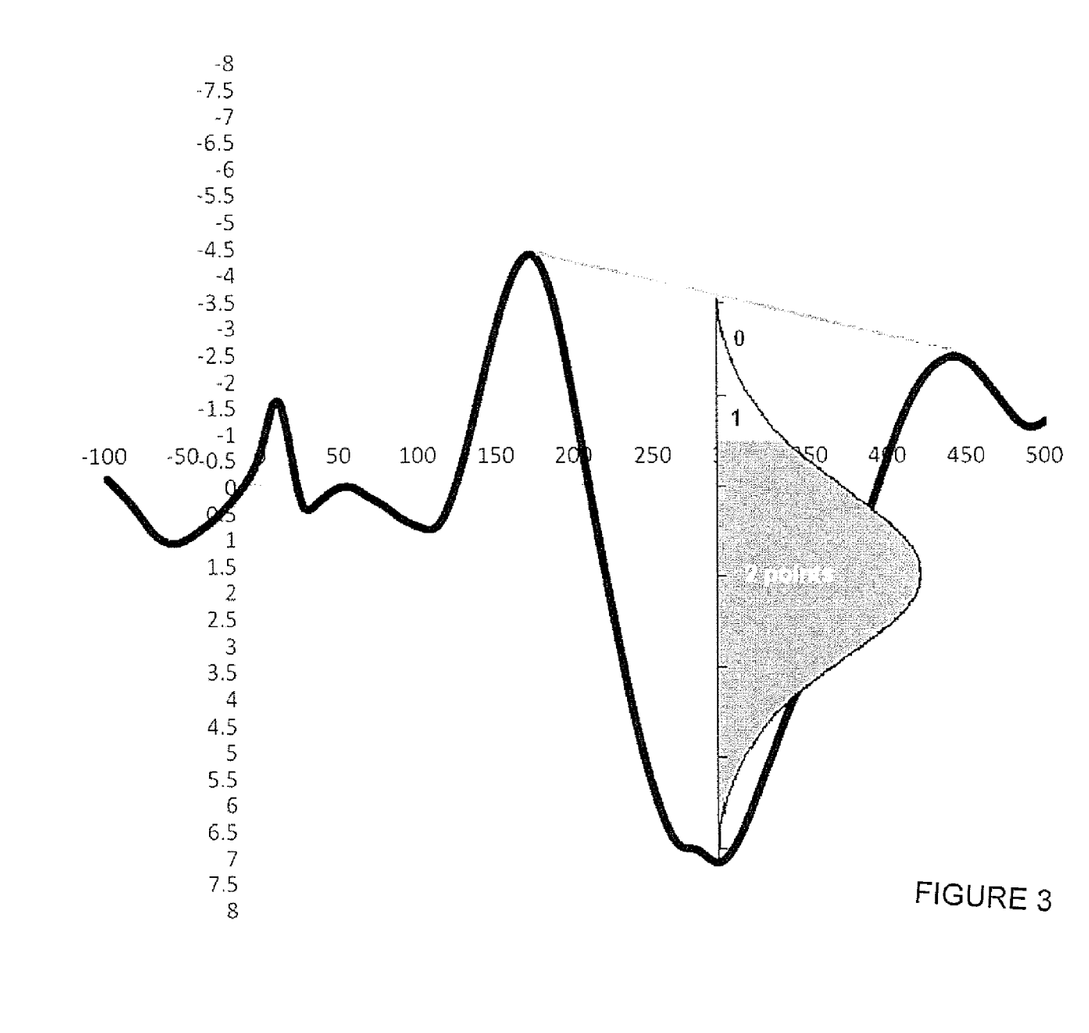
FIG. 3 is an illustration of Dx point allotment for an amplitude measurement made by the inferred baseline (IB) method for the P300 to infrequent loud tones by comparison to the normative database. A normal curve is overlaid vertically upon the ERP waveform to demonstrate the Dx points that would be allotted for a P300 whose amplitude falls within abnormal, borderline, and normal amplitude ranges.

As shown in FIG. 3, points in the Dx score are allotted to each of the 5 areas of processing based on a statistical assessment of differences between the patient's ERP peak amplitudes and normative values, such as mean and standard deviations, from a database. These values are provided in the software. In the present embodiment of the method, the normative sample is divided into regions of normal, borderline, and abnormal peak amplitude for each of the ERP components used to assess cognitive function. For instance, the threshold can be set wherein P1-N1 amplitudes that are more than 3 standard deviations below the mean amplitude from the normative sample are considered "abnormal". For this abnormal response, no points may be allotted for sensory processing. If the measured P1-N1 amplitude is more than 2, but less than 3 standard deviations below the mean amplitude from the normative sample, the response may be considered "borderline". For this borderline response, 1 point can be allotted for sensory processing. However, if P1-N1 amplitude is less than 2 standard deviations below the mean amplitude from the normative sample, this normal response can receive full points (by this example, 2 points). Similar distinctions can be made for perceptual processing (MMN), attention/alerting mechanisms (P300), memory retrieval (N2, P300), and language processing (N400).

ERP responses in severely brain damaged patients do not necessarily follow a strict hierarchy in which an absence of lower-level sensory ERPs means that higher-level verbal ERPs will also be lacking. Thus, it is important to utilize a use a whole battery of ERP indicators—it is not appropriate to declare a patient cortically non-responsive as a consequence of a negative result for a single ERR Hierarchical paradigms also have two other important advantages: they provide a level of consistency when multiple tasks all yield negative results, and they can provide useful information about cognitive specificity when only specific responses are missing (Monti et al., 2009). Thus, the overall Dx score can be used as a general index of the cognitive functions that contribute to conscious awareness, or the score can be broken down into its subcomponents, bearing in mind that a negative result does not constitute conclusive evidence for a lack of processing at any specific level.

The reliability (Rx) and validity (Vx) scores are allotted based on the features of the ERP components and the repeatability and/or consistency of their waveform characteristics. In the current embodiment of the method, this means that if repeatable components are observed in more than one waveform, points are allotted to the Rx score. For instance, the P1-N1 ERP components are observable in response to the onset of virtually any sound. If the P1-N1, therefore, is found in response to both the standard tonal stimuli and intensity deviant tonal stimuli, points may be allotted to the Rx score. Similar calculations are done for the Vx score, whereby a "fit to template" is calculated as a normalized measure of percent difference from the normative waveform over a specific time period.

The prognostic (Px) score is calculated using the statistical relationships between waveform features and patient outcomes. In one embodiment of the method, this is determined using a classification approach to assess fit to prior patient data divided on the basis of recovery versus no recovery for a specific indicator. For instance, a statistical analysis in the form of a cluster analysis can yield specific ERP waveform features that tend to appear in patients that recover, versus those that do not recover. It should be noted that a variety of different statistical tests could be used to quantify the extent to which evoked response waveform features predict patient outcomes. Although the current embodiment is described to use a classification approach, other statistical tests, such as regression analyses, remain of interest. Points in the Px score are allotted based on the number and size of the features in the waveform data that are predictive of patient outcomes.

Figure 4A:
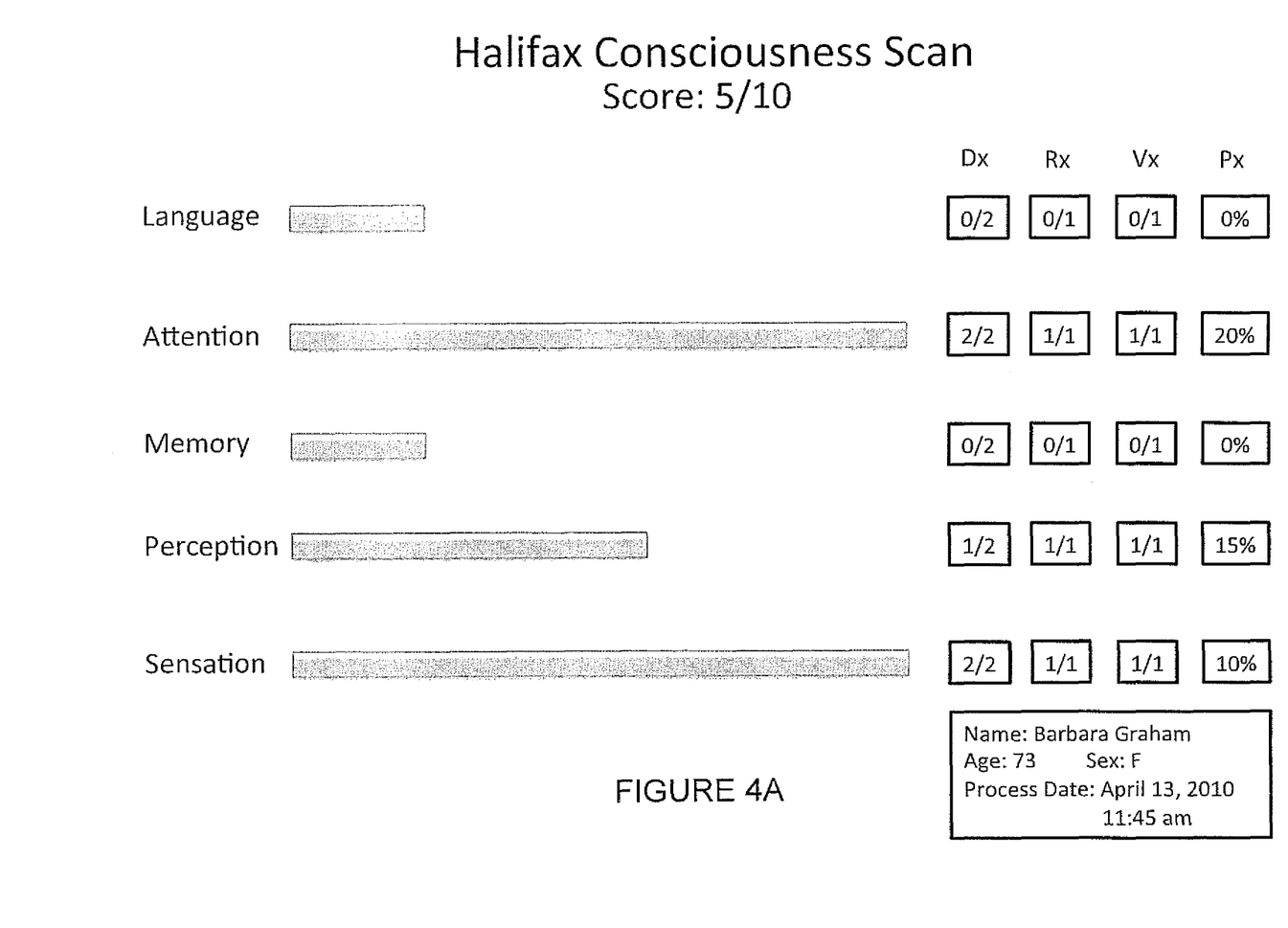
FIG. 4A is an illustration of the device output of the test.
Figure 4B:
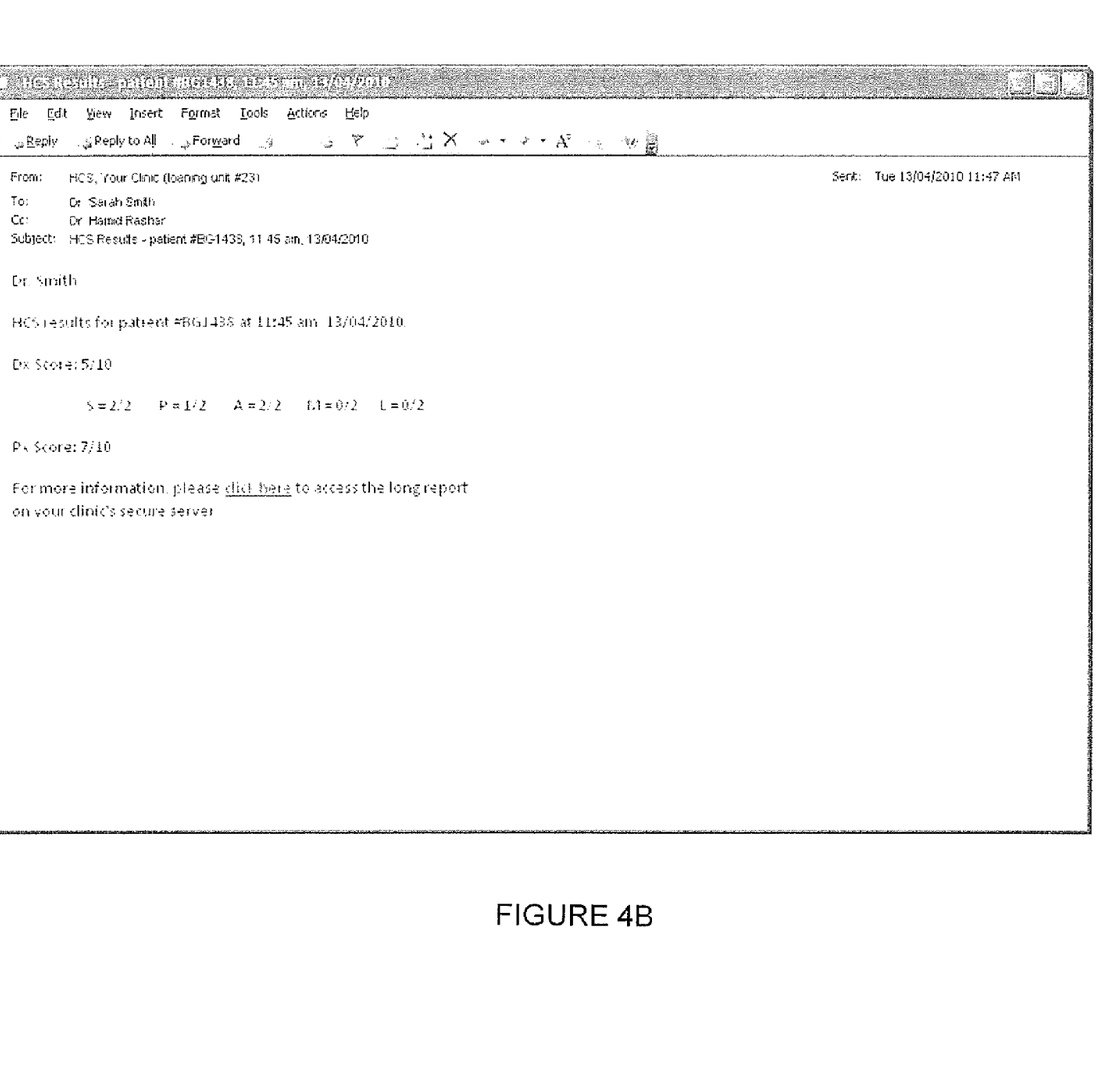
FIG. 4B is an illustration of an e-mail of the results to the attending physician(s).

The scores (Dx, Rx, Vx, Px) must be communicated to caregivers and health care workers. This communication takes place via graphical output that is sent to the screen of a portable device, and outputs that are integrated with current communications technologies. A plurality of reports, such as abbreviated "Short Reports", as shown in FIGS. 4A and 4B, and detailed "Long Reports", as set out hereinafter and shown in FIG. 5, will be communicated via telecommunications networks for rapid dissemination and easy integration into the Critical Care Cascade.

Figure 5:
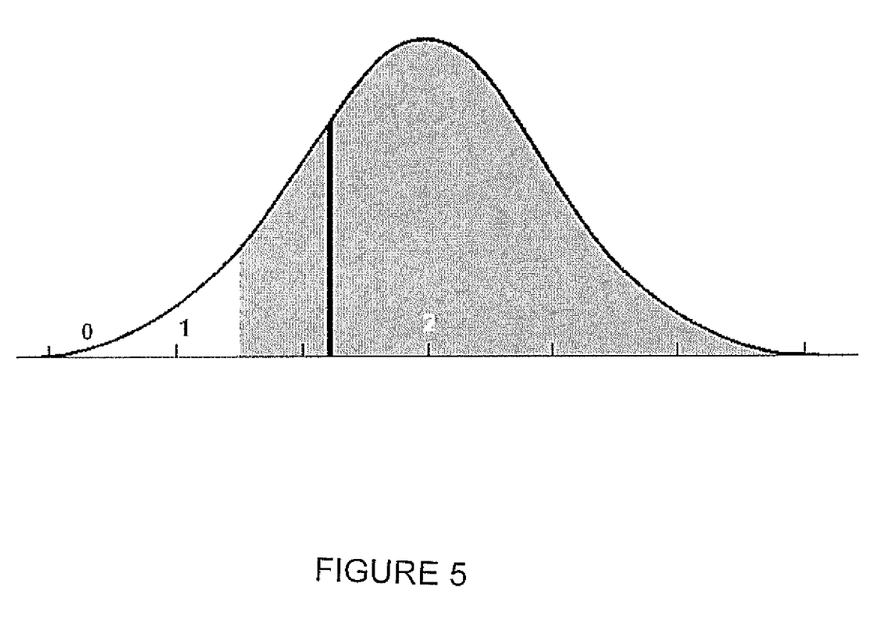
FIG. 5 is a graph taken from a more detailed Long Report that accompanies the e-mail to the attending physician(s).

The following together with graphs similar to that shown in FIG. 5 provides a copy of a typical more detailed Long Report that accompanies the e-mail to the attending physician(s). To maintain patient confidentiality, such a Long Report can be forwarded to a health care institution's secure server for later access.

| Detailed Report | |
|---|---|
| Patient #BG1438 - Barbara Graham | |
| Test Date | 13 Apr. 2010, 11:45 am |
| Age | 73 |
| Gender | F |
| Care Setting | Home |

-continued

| Detailed Report | | | | |
|---|---|---|---|---|
| Contact | Shelly Graham, daughter Home: (111) 555-2452 | | Cell: (111) 555-1976 | |
| Diagnosis | stroke | | | |

| | HCS Score Breakdown | | | |
|---|---|---|---|---|
| | Dx | Rx | Vx | Px |
| Total | 5/10 | 3/10 | 5/5 | 7/10 |
| Sensory | 2/2 | 1/1 | 1/1 | |
| Perceptual | 1/2 | 1/1 | 1/1 | |
| Attention | 2/2 | 1/1 | 1/1 | |
| Memory | 0/2 | 0/1 | 1/1 | |
| Language | 0/2 | 0/1 | 1/1 | |

Diagnostic (Dx) Score: 5/10

The Dx score refers to the number of indicators of conscious awareness that are present, and the normality of their amplitudes.

FIG. 5, which illustrates a normative distribution for an evoked response of interest, with shading that designates the "normal", "borderline", and "abnormal" regions of the normative distribution, along with numerical indications of the points allotted in each of those regions. The placement of the dark black bar indicates the size of the patient's evoked response. In a plot similar to FIG. 5, there is shown a Sensory Score: 2/2, percentile rank 27, where the sensory score indicates whether the patient demonstrates ERP responses elicited during sensory processing. Such ERP responses include P1, N1, and P2. The sensory ERP response is within the normal range (indicated by a bolded line).

In a plot similar to FIG. 5, there is shown a Perceptual Score: 1/2, percentile rank 4, where the perceptual score indicates whether the patient demonstrates ERP responses elicited only by sounds that have reached the level of sensory memory, and have been organized according to perceptual rules. Such ERP responses include the mismatch negativity (MMN) and N2. The perceptual ERP response is within the borderline range.

In a plot similar to FIG. 5, there is shown an Attention Score: 2/2, percentile rank 76. The attention score indicates whether the patient demonstrates ERP responses elicited by the activation of alerting systems and context updating triggered by orienting sounds. Such ERP responses include the P300. The attentional ERP response is within the normal range.

In a plot similar to FIG. 5, there is shown a Memory Score: 0/2, percentile rank 0.6. The memory score indicates whether the patient demonstrates ERP responses elicited by alerting systems and context updating triggered by personally-relevant, learned sounds (such as their name) via memory retrieval. Such ERP responses include the P300. The memory ERP response is absent.

In a plot similar to FIG. 5, there is shown a Language Score: 0/2, percentile rank 0.8. The language score indicates whether the patient demonstrates ERP responses elicited by linguistic stimuli that are being processed for semantic meaning within the context of sentences. Such ERP responses include the N400. The language ERP response is absent.

Reliability (Rx) Score: 3/10

The Rx score refers to the repeatability of ERP indices across different stimulus conditions. It provides an index of the robustness of the observed response.

Sensory Score: 1/1

The sensory response was observed in more than one condition.

Perceptual Score: 1/1

The perceptual response was observed in more than one condition.

Attention Score: 1/1

The attention response was observed in more than one condition.

Memory Score: 0/1

The memory response was absent.

Language Score: 0/1

The language response was absent.

Validity (Vx) Score: 315

The Vx score refers to the goodness of fit of the ERP waveform to the norm. It provides an index of the conformity of the ERP response to expected waveform characteristics.

Sensory Score: 1/1

The sensory ERP resembles a typical normal response.

Perceptual Score: 1/1

The perceptual ERP resembles a typical normal response.

Attention Score: 1/1

The attention ERP resembles a typical normal response.

Memory Score: 0/1

The memory ERP was abnormal.

Language Score: 0/1

The language ERP was abnormal.

Prognostic (Px) Score: 7/10

The patient demonstrates 70% of the ERP features that are typical of stroke patients who later recover wakeful awareness.

The invention claimed is:

1. A method for analysis of the extent of conscious awareness and/or likelihood of recovery of a patient comprising:
   applying to the patient a sensory stimulus sequence generated by a stimulator;
   while applying the stimulus sequence, carrying out an EEG or MEG on the patient to record waveform signals from an array of sensors on, in, or near the head of the patient;
   wherein the stimulus sequence comprises a compressed stimulus sequence that elicits at least five indicators across a spectrum of brain functions comprising sensory processing, perceptual processing, attention/alerting mechanisms, memory retrieval, and language;
   using software provided in a processor to process the waveform signals in order to locate waveform peaks, identify the evoked responses contained in the waveform and obtain quantitative measures of these evoked responses;
   wherein the software uses an automated peak localization method that performs a mathematical decomposition of an averaged waveform to identify all peaks in the waveform signals; and wherein the software then applies identification criteria to choose a candidate peak of interest;
   and using the software to generate and communicate scores based on the quantitative measures that are indicative of the extent of conscious awareness and/or likelihood of recovery of the patient.

2. The method according to claim 1 wherein the compressed stimulus sequence takes less than 5 minutes.

3. The method according to claim 1 wherein the software generates scores comprising a diagnostic score and wherein points in the diagnostic score are allotted based on said evoked responses related to said plurality of brain functions.

4. The method according to claim 1 wherein the software generates scores comprising a diagnostic score and wherein points in the diagnostic score are allotted based on the statistical assessment of differences between quantitative measures of the patient's evoked responses and normative values from a database.

5. The method according to claim 1 wherein the software generates scores comprising a prognostic score and wherein points in the prognostic score are allotted based on the statistical relationships between averaged waveform features and historical outcomes of patients diagnosed with the same condition.

6. The method according to claim 1, wherein the peak localization method identifies all peaks by determining the zero crossings of the averaged waveform's first and second derivatives, yielding peak and inflection points of the waveform's curvature.

7. The method according to claim 1, wherein the peak localization method employs an amplitude thresholding method whereby small peaks are rejected from further analysis.

8. The method according to claim 1, wherein the identification criteria are applied that describe generic ERP/ERF component characteristics based on several basic features, such as experimental condition, latency, and polarity.

9. The method according to claim 1, wherein the peak localization method takes into account the peak's shape and curvature, its relationship to peaks in other averaged waveforms for different experimental conditions, and the shape and curvature of the averaged waveform between this peak and its neighboring peak.

10. The method according to claim 1, wherein the software uses an adaptive pattern recognition process to perform a series of automated and iterative adjustments to the previously described identification criteria to accommodate, where possible, the differences between individuals.

11. The method according to claim 1, wherein the pattern recognition process to examine relationships with peaks in waveforms for different experimental conditions, such as relative amplitudes and crossover points between the waveforms.

* * * * *